United States Patent [19]
Armstrong et al.

[11] Patent Number: 5,713,366
[45] Date of Patent: Feb. 3, 1998

[54] METHOD AND APPARATUS FOR DUAL CHAMBER CARDIAC ANALYSIS

[75] Inventors: Randolph K. Armstrong, Missouri City; Eliot L. Ostrow, Sugar Land, both of Tex.

[73] Assignee: Sulzer Intermedics Inc., Angleton, Tex.

[21] Appl. No.: 714,241

[22] Filed: Sep. 16, 1996

[51] Int. Cl.⁶ .................................. A61B 5/0464
[52] U.S. Cl. ..................... 128/697; 128/705; 607/14
[58] Field of Search ................... 607/4, 5, 9, 30, 607/32, 60, 14; 128/697, 702, 705, 710

[56] References Cited

U.S. PATENT DOCUMENTS

| | | | |
|---|---|---|---|
| 4,791,936 | 12/1988 | Snell et al. | 128/697 |
| 4,800,883 | 1/1989 | Winstrom . | |
| 5,309,919 | 5/1994 | Shell et al. | 128/697 |
| 5,327,900 | 7/1994 | Mason et al. | 128/705 |
| 5,507,780 | 4/1996 | Finch | 128/705 X |
| 5,518,001 | 5/1996 | Snell | 128/697 |
| 5,529,579 | 6/1996 | Alt et al. | 607/36 |
| 5,545,182 | 8/1996 | Stotts et al. | 607/5 |

OTHER PUBLICATIONS

Res-Q Physician's Manual, Nov. 1995.

*Primary Examiner*—Jeffrey R. Jastrzab
*Attorney, Agent, or Firm*—John R. Merkling

[57] ABSTRACT

A method and apparatus for analyzing cardiac information involves recording both atrial and ventricular information related to a recognized event. This information can then be transmitted by telemetry to the physician and graphed on a common graph which plots both atrial and ventricular information over the time period of the event. This technique allows greater ability to discern the true nature of these events, including whether a given event is a sinus tachycardia due to exercise or a ventricular tachycardia which might necessitate treatment. Therefore, the present invention enables more accurate analysis of cardiac information and thereby makes possible the more appropriate application of treatment.

7 Claims, 3 Drawing Sheets

METHOD AND APPARATUS FOR DUAL CHAMBER CARDIAC ANALYSIS

FIELD OF OUR INVENTION

Our invention relates generally to implantable pacemakers and implantable cardioverter/defibrillators and more particularly to methods and apparatus for analyzing atrial and ventricular rates.

BACKGROUND OF OUR INVENTION

In conventional pacemakers and implantable cardioverter/defibrillators or ICDs, it is well known to monitor the ventricle to determine the frequency or rate of heart contractions. Physicians are adept at analyzing this information to determine the nature of a variety of heart conditions. For example, based on the rate of ventricular contractions, physicians diagnose that a tachyarrhythmia has occurred.

However, the inventors of the present application have appreciated that in a number of cases the information obtained by solely monitoring ventricular rate and interval can be misleading. For example, in some instances a sinus tachycardia brought on by extreme exercise could be interpreted as ventricular tachyarrhythmia. Such a misdiagnosis could result in inappropriate therapy. Physicians tolerate such a misdiagnosis by applying shock to patients in the interest of safety whenever there is a questionable situation. However, unnecessary shocks decrease the longevity of the implantable device and cause unnecessary patient suffering. Similarly, physicians can raise the boundary of the preset level that is recognized by the ICD as a tachyarrhythmia. However, it is possible to thereby fail to treat tachyarrhythmias which may occur at rates beneath the raised tachyarrhythmia treatment level.

There are some instances where atrial fibrillation may not be detected and the physician may not be aware that a fibrillation has occurred. Even with historical sensing of ventricular events, there may be some abnormalities in the ventricular rates that accompany atrial fibrillation that may not be sufficiently severe to trigger the recording of the event. In other words, the increase in rate of ventricular contractions may not be sufficiently substantial to cause the atrial fibrillation event to even be recorded. This may occur where there is a conduction block in connection with the atrial fibrillation.

Therefore, it would be highly desirable to have a more reliable way for monitoring cardiac abnormalities so that only the appropriate treatment regimens may be applied to the greatest possible extent.

SUMMARY OF OUR INVENTION

In accordance with one embodiment of our invention, a system is provided which enables both atrial and ventricular heart rates or intervals to be monitored on a historical basis. When an abnormality is sensed, the event is recorded for subsequent playback by the physician through telemetry communications.

When the physician is armed with both atrial and ventricular information about the recorded event, the physician can more accurately diagnose the condition. This avoids not only the failure to provide needed therapy but also the inadvertent application of unnecessary electrical therapy.

DESCRIPTION OF A PREFERRED EMBODIMENT

Figure 1:
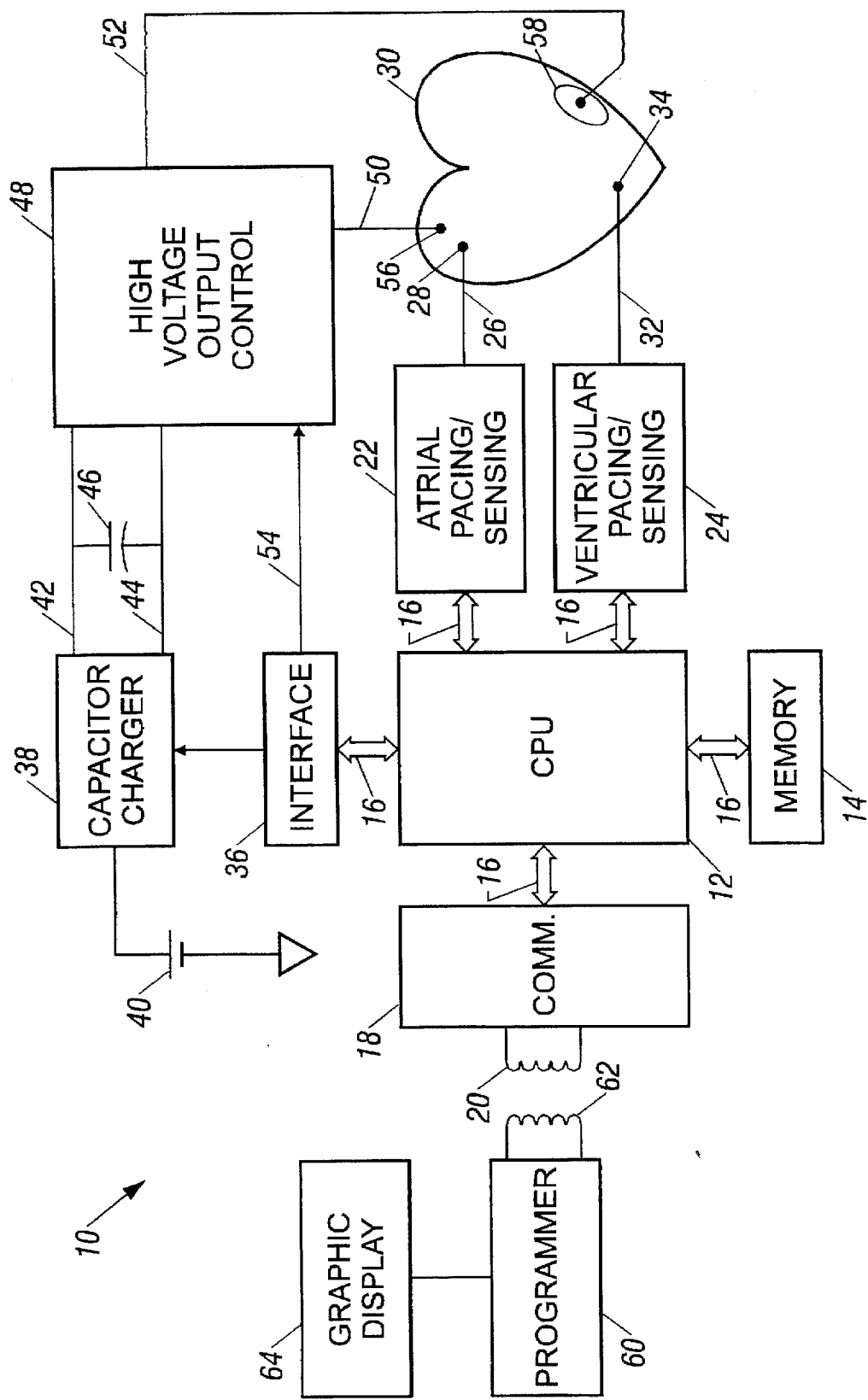
FIG. 1 is a block diagram of one embodiment of our invention.

Referring to FIG. 1 wherein like reference characters are used for like parts throughout the several views, an implantable defibrillator 10 in accordance with the present invention is controlled by a digital central processing unit (CPU) operated under the control of software stored in memory unit 14. Central processing unit 12 and memory unit 14 communicate in a well known fashion over data and address bus 16.

The central processing unit 12 may be programmed by an external programmer 60 that communicates with the defibrillator 10 via the communications unit 18. The antenna coil 20 connected to the communications unit 18 receives electromagnetic energy radiated by a transmitter portion 62 of the external programmer 60 with the electromagnetic energy being modulated to convey programming instructions. The received energy is demodulated in communications unit 18 and the data and programming instructions are passed on to CPU 12 over data and address bus 16. The antenna coil 20 also serves to radiate modulated electromagnetic energy from transmitter portion of communications unit 18 to transfer data to the external programmer 60 which may include a printer or graphic display 64. Such data can convey information about the parameters and modes of the defibrillator 10, and about sensed physiological information.

Atrial pacing/sensing unit 22 and ventricular pacing/sensing unit 24 communicate with the CPU unit 12 over data and address bus 16 to provide dual chamber pacing therapies in addition to the cardioversion and defibrillation therapies which are the principal objectives of defibrillator 10.

An atrial lead 26 having one or more electrodes 28 for placement in an atrial chamber of the heart is electrically connected to atrial pacing/sensing unit 22. The lead 26 delivers pacing pulses to the atrium, and senses naturally occurring depolarization signals and other signals for use by the CPU unit 12 to regulate therapy.

A ventricular lead 32 having one or more electrodes 34 for placement in a ventricular chamber of the heart is electrically connected to ventricular pacing/sensing unit 24 for delivering pacing pulses to the ventricle, and for sensing naturally occurring depolarization signals and other signals for use by CPU unit 12 to regulate therapy. It should be understood that leads 26 and 32 as shown are merely representative of a typical dual chamber pacing arrangement, and may be arranged for bipolar or unipolar pacing, or other pacing modes as are known in the art.

Defibrillation therapy is initiated by control signals from CPU unit 12 applied over data and address bus 16 to the high voltage interface 36. Interface 36, among other things, isolates the high voltage portions of defibrillator 10 from CPU unit 12 and the other low voltage circuitry. Control circuits buffered by interface 36 are applied to capacitor charger unit 38 having an input line connected to a battery 40 and a pair of high voltage output lines 42 and 44 connected to a high voltage energy storage capacitor 46. It should be appreciated that while the battery 40 is shown as connected only to capacitor charger 38 in the simplified block diagram of FIG. 1, the battery 40 also supplies power for all the active devices in the digital and analog circuitry of the defibrillator 10.

Lines 42 and 44 also connect energy storage capacitor 46 to high voltage output control unit 48, which controls the delivery of high voltage charge from the capacitor 46 to defibrillation leads 50 and 52 in response to control signals received from interface 36 on line 54. Leads 50 and 52 are provided with one or more endocardiac electrodes 56 and one or more patch electrodes 58. It should be understood that leads 50 and 52 as shown are merely representative of typical defibrillation lead arrangements and may be arranged differently according to other defibrillating modes as are known in the art.

In operation, a microprocessor or CPU 12 is programmed to store in memory 14 any event which meets predetermined parameters. These events would normally be abnormalities which might be useful in diagnosis. The physician may for example set a number of heart rate levels which trigger the determination that an event has occurred when these levels are exceeded. Thus, the CPU automatically stores in memory 14 any event which meets the predetermined parameters.

In accordance with the present invention, atrial and ventricular sensing is utilized. Advantageously both the atrial and ventricular information is plotted on the external graphic display 64 on a common plot whereby atrial and ventricular rates or intervals are plotted over time for each recorded event.

Figure 2:
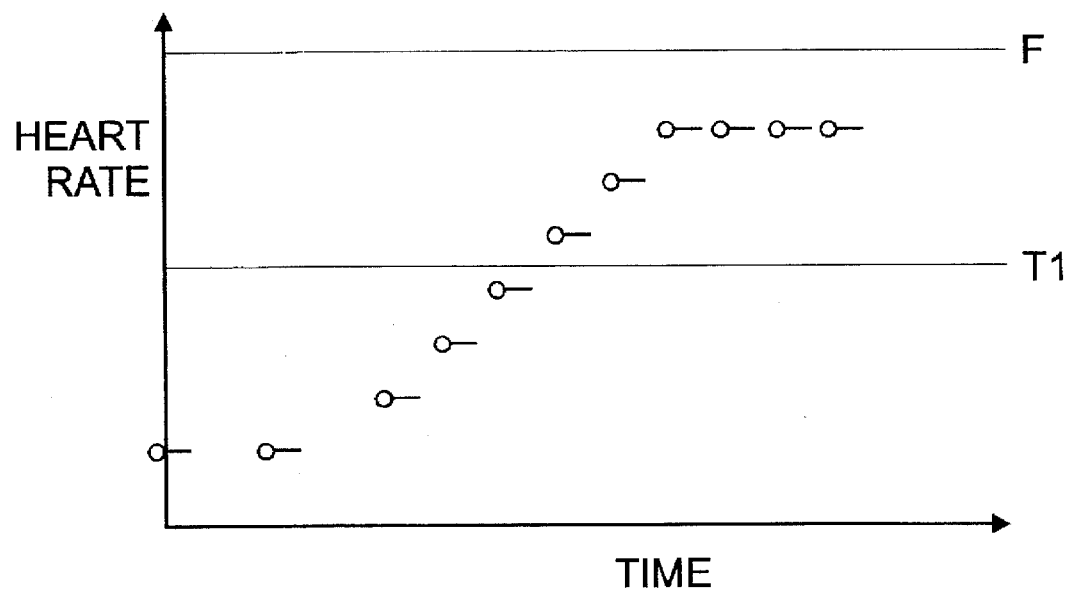
FIG. 2 is an exemplary printout of a recorded event which was a sinus tachycardia due to exercise.
Figure 3:
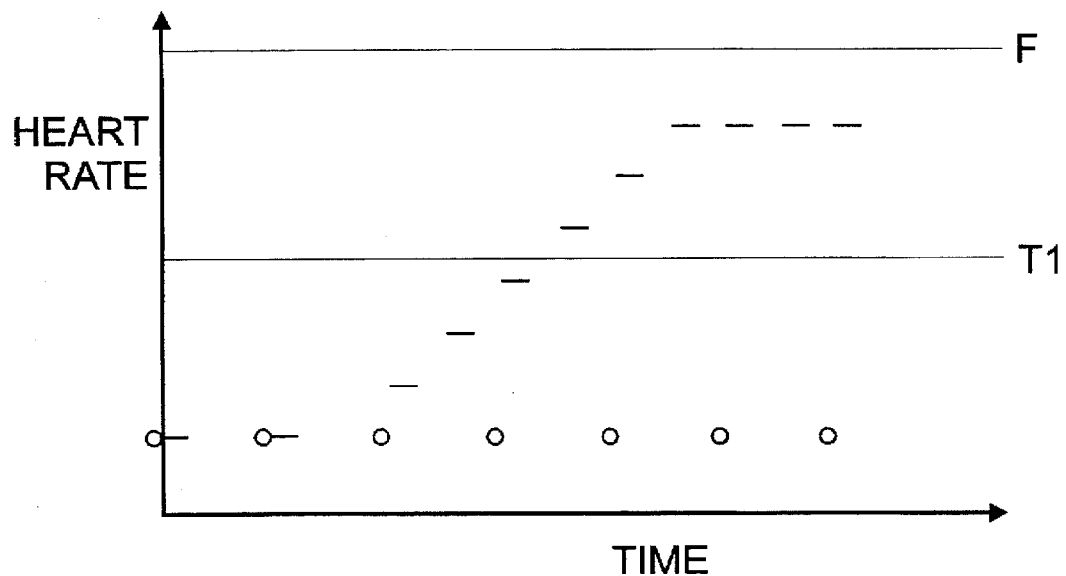
FIG. 3 is an exemplary printout of a recorded event which was a ventricular tachycardia.
Figure 4:
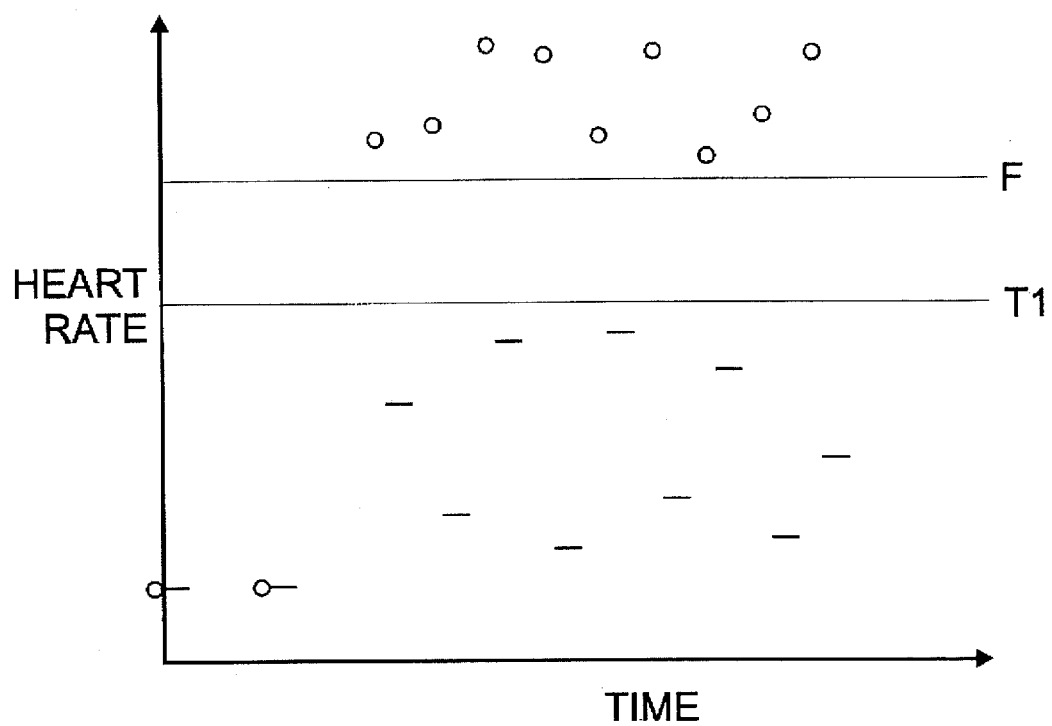
FIG. 4 is an exemplary printout of an atrial fibrillation with conduction block.

Through the provision of both atrial and ventricular information, the physician may, in some instances, be able to make a more accurate diagnosis and may be able to apply therapy in a more appropriate fashion. For example, referring to FIG. 2, a plot in accordance with the present invention is provided. The vertical axis is heart rate and the horizontal axis shows the time for an exemplary event. The level T1 is a hypothetical head rate which was preprogrammed by the physician causing the event to be recorded because the level T1 was exceeded. The level F is a preprogrammed level by the physician which is recognized as a fibrillation. In FIGS. 2 through 4, both atrial and ventricular heart rates are plotted with the zeros being the atrial rate and the dashes being the ventricular rate.

In FIG. 2, both atrial and ventricular rates rise above the level T1 set by the physician. Thus, the physician could have preprogrammed a shock to occur when the level T1 is exceeded. However, the atrial information indicates that both atrial and ventricular rates went up. This means that the event is sinus tachycardia due to stress or exercise. In such a situation electrotherapy would not be appropriate.

This can be better understood from FIG. 3 which shows both the atrial and ventricular rate information for a ventricular tachycardia. From the atrial information it is evident that the event is a ventricular tachycardia because the atrial rate is unchanged. With conventional techniques, the physician would only have the ventricular information to rely upon. There is relatively little difference between the ventricular information for a sinus tachycardia, as shown in FIG. 2, and a ventricular tachycardia, as shown in FIG. 3. Thus the possibility of misdiagnosis is real and this is particularly so when automated diagnosis and therapy application techniques are utilized.

FIG. 4 shows an atrial fibrillation. Atrial fibrillations would, under conventional techniques, have been largely ignored since only ventricular event information is recorded.

It can be seen that the ventricular rate is not particularly high and in most instances could well be ignored. However, only with the provision of the atrial information would the physician appreciate that an atrial fibrillation occurred. In this instance, using the conventional techniques, therapy would not have been applied when in fact electro-therapy might well have been appropriate.

While the present invention has been described with respect to a limited number of embodiments, those skilled in the art will appreciate a variety of embodiments in accordance with the present invention. Therefore, the appended claims are intended to cover all such modifications and variations that fall within the true spirit and the scope of present invention.

We claim as our invention:

1. A method for monitoring cardiac signals comprising the steps of:

recording a beat-by-beat atrial rate as said atrial rate varies over time when a cardiac rate exceeds a certain level;

recording a beat-by-beat ventricular rate as said ventricular rates varies over time when the ventricular or atrial rate exceeds a certain level;

plotting the atrial and ventricular rates together on the same plot over time, on a beat-by-beat basis exclusive of other information from said cardiac signals; and providing an indication of types of tachycardia based on said plot.

2. The method of claim 1 including the step of selecting at least one ventricular or atrial as said cardiac rate.

3. The method of claim 2 including the step of recording said atrial and ventricular rates in an implantable device.

4. The method of claim 3 including the step of transmitting said recorded rates to a receiver outside the implantable device, and receiving said recorded rates in an external device.

5. The method of claim 4 including the step of determining treatment based on a comparison of the plotted ventricular and atrial rates.

6. A system for dual chamber cardiac analysis comprising:

an implantable device including:

a device for detecting a cardiac event, said cardiac event comprising a plurality of beats;

means for determining an atrial rate and a ventricular rate for each beat of said said detected cardiac event; and a memory for recording said atrial and ventricular rates;

a transmitter connected to said memory for transmitting said atrial and ventrical rates; and an external machine including a telemetry system for receiving said transmitted rates and a display device for simultaneously graphing points representative of said atrial and ventricular rates recorded by said memory exclusive of other information on said cardiac event versus time on a beat-by-beat basis to provide an indication of types of tachycardia based on said graphed points.

7. The system of claim 6 wherein said external machine includes programming means for setting rate levels that determine when a cardiac event has occurred and wherein said implantable device includes a receiver and means for receiving said rate levels and wherein said memory comprises means for recording whenever said rates exceed said received rate levels.

* * * * *